US009243892B2

(12) United States Patent
Tochino

(10) Patent No.: US 9,243,892 B2
(45) Date of Patent: Jan. 26, 2016

(54) PARTICLE ANALYTICAL DEVICE

(71) Applicant: HORIBA, Ltd., Kyoto (JP)

(72) Inventor: Shigemi Tochino, Kyoto (JP)

(73) Assignee: HORIBA, LTD. (JP)

(*) Notice: Subject to any disclaimer, the term of this patent is extended or adjusted under 35 U.S.C. 154(b) by 346 days.

(21) Appl. No.: 13/767,980

(22) Filed: Feb. 15, 2013

(65) Prior Publication Data

US 2013/0218519 A1     Aug. 22, 2013

(30) Foreign Application Priority Data

Feb. 16, 2012  (JP) .................... 2012-032161

(51) Int. Cl.
   G01B 7/12      (2006.01)
   G01B 11/10     (2006.01)
   G01N 15/02     (2006.01)
   G01N 15/00     (2006.01)

(52) U.S. Cl.
   CPC .......... G01B 11/105 (2013.01); G01N 15/0211 (2013.01); G01N 2015/0038 (2013.01); G01N 2015/0222 (2013.01)

(58) Field of Classification Search
   USPC ........................................................ 702/157
   See application file for complete search history.

(56) References Cited

U.S. PATENT DOCUMENTS

| | | | | |
|---|---|---|---|---|
| 4,676,640 A | * | 6/1987 | Briggs | 356/317 |
| 4,788,443 A | * | 11/1988 | Furuya | 250/574 |
| 4,830,494 A | * | 5/1989 | Ishikawa et al. | 356/336 |
| 5,257,087 A | | 10/1993 | Furuya | |
| 5,583,635 A | * | 12/1996 | Miura et al. | 356/338 |
| 2003/0142311 A1 | * | 7/2003 | Molter et al. | 356/339 |
| 2009/0091756 A1 | * | 4/2009 | Yamaguchi et al. | 356/336 |

FOREIGN PATENT DOCUMENTS

| | | |
|---|---|---|
| GB | 1263586 | 2/1972 |
| GB | 1516198 | 6/1978 |
| JP | 60-35882 U | 3/1985 |
| JP | 5-48359 U | 6/1993 |
| JP | 9-236411 A | 9/1997 |
| JP | 2000-9644 A | 1/2000 |
| JP | 2005-249759 A | 9/2005 |
| JP | 2008-180691 A | 8/2014 |

OTHER PUBLICATIONS

Search Report under Section 17(5) for U.K. patent application No. 1302604.2 dated May 8, 2013.
Summary of the Decision to Grant a Patent, issued in Japanese Application No. 2012-032161, dated Dec. 12, 2013, with English summary.

* cited by examiner

*Primary Examiner* — Paul D Lee
(74) *Attorney, Agent, or Firm* — Cantor Colburn LLP

(57) ABSTRACT

A particle analytical device comprises a light receiving part that receives the scattered light emitted from the particle group and that outputs an electric current signal, a data processing part that processes data based on time series data of a number of pulses obtained by the electric current signal, and a control part that halts a movement of the light receiving part in case that the overcurrent is detected based on the electric current signal and that restarts the movement of the light receiving part after a predetermined time passes and is characterized by that the data processing part holds the time series data until the light receiving part is halted and processes the data after the movement of the light receiving part is restarted by the use of the held time series data and the time series data obtained after the restart.

4 Claims, 7 Drawing Sheets

PARTICLE ANALYTICAL DEVICE

CROSS REFERENCE TO RELATED APPLICATIONS

Priority under 35 U.S.C. §119(a) is claimed from Japanese Application No. 2012-032161, filed 16 Feb. 2012, the disclosure of which is also incorporated herein by reference.

FIELD OF THE ART

This invention relates to a particle analytical device that analyzes physicality of a particle based on the scattered light due to the particle by irradiating the light such as the laser.

BACKGROUND ART

In accordance with the recent development of nanotechnology, a demand is growing for an extremely micro particle (hereinafter called as a single nanoparticle) of a single nanometer (1~10 nm). In case of manufacturing the single nanoparticle with high accuracy, since a grinding method has limitations, a method for producing a single nanoparticle by growing a crystal has been developing recently. In this case, it is necessary to measure a diameter of a particle during a process of growing the crystal in real time in order to control, for example, a particle diameter.

As a method for measuring a diameter of a particle among analyzing particles known are various methods such as a laser diffraction method and a centrifugal sedimentation method, however, practically from a view point of a performance and a cost, a photon correlation method that is based on a dynamic scattering theory is one of the most effective methods in order to measure a diameter of a single nanoparticle.

A particle diameter distribution measurement device by the use of the photon correlation method based on the dynamic scattering theory irradiates the laser light on particles that are making the Brownian motion in a sample solution, receives the scattered light due to the particle by the use of a photoelectron multiplier, makes auto-correlation data based on a pulse obtained by shaping a waveform of an electric current signal output by the photoelectron multiplier and calculates particle diameter distribution of a particle group based on the auto-correlation data.

In accordance with the particle diameter distribution measurement device having the above arrangement, in case that the scattered light enters into the photoelectron multiplier due to, for example, a foreign material whose particle diameter in a sample solution is big, there might be a case that an overcurrent that is more than or equal to an allowable value is produced in the photoelectron multiplier. In case that the overcurrent is produced, since the photoelectron multiplier is desensitized and deteriorated, an absolute value of a negative high voltage applied to the photoelectron multiplier is decreased or applying the negative high voltage is ceased in order to halt the measurement at a time when the overcurrent is produced (for example, the patent documents 1 and 2).

In accordance with this kind of the particle diameter distribution measurement device, in case that the measurement is halted in midstream, time series data of a number of pulses that are continuous from initiation of the measurement is broken at the time. As a result of this, even though the measurement is restarted after this time, since there exists no time series data of the pulse number from the initiation of the measurement to the halt of the measurement due to the overcurrent, it becomes impossible to produce the auto-correlation data. Then, it becomes necessary for a user to restart the measurement of the scattered light from the beginning.

PRIOR ART DOCUMENT

Patent Document

Patent document 1: Japanese Examined Utility Model Application Publication No. Sho 60-35882
Patent document 2: Japanese Examined Utility Model Application Publication No. Hei 5-48359

DISCLOSURE OF THE INVENTION

Problems to be Solved by the Invention

The present claimed invention intends to solve all of the problems and a main object of this invention is to make it possible to avoid damage of the particle analytical device that analyzes physicality of a particle based on scattered light due to the particle by irradiating light such as laser and to restart the analysis rapidly in case that abnormal occurs in the scattered light.

Means to Solve the Problems

More specifically, the particle analytical device in accordance with this invention comprises a light irradiation part that irradiates the light toward a particle group that moves in a dispersion medium, a light receiving part that receives the scattered light emitted from the particle group on which the light from the light irradiation part is irradiated and that outputs an electric current signal, a data processing part that processes data concerning particle analysis based on time series data of a number of pulses obtained by the electric current signal output by the light receiving part, an overcurrent detecting part that detects flowing of an overcurrent in the light receiving part based on the electric current signal output by the light receiving part, and a control part that halts a movement of the light receiving part in case that the overcurrent detecting part detects the overcurrent and that restarts the movement of the light receiving part after a predetermined time passes from a time when the movement of the light receiving part is halted, and is characterized by that the data processing part holds the time series data until the halt at a time when the movement of the light receiving part is halted and processes the data after the movement of the light receiving part is restarted by the use of the held time series data and the time series data obtained after the restart.

The overcurrent in this embodiment indicates an electric current that flows due to receiving the scattered light so that receiving the subsequent light is precluded, namely, an electric current that is both smaller than an electric current (a prebreakdown current) that breaks the light receiving part and more than or equal to a predetermined electric current. Concretely, an electric current that is both more than or equal to a predetermined electric current that is set as, for example, about 80% of the electric current amount of the prebreakdown current and less than the above-mentioned prebreakdown current is set as the overcurrent. The overcurrent is detected in a case that the predetermined electric current is set as, for example, 80% of the prebreakdown current and the electric current amount that is based on the electric current signal output by the light receiving part is more than or equal to the predetermined electric current amount.

In accordance with this arrangement, since the movement of the light receiving part is halted in case that the overcurrent detecting part detects that the overcurrent flows in the light receiving part, it is possible to prevent the light receiving part from getting damaged. In addition, since the movement of the light receiving part is restarted after the predetermined period of time, it is possible to analyze the particle quickly. Furthermore, since the time series data is held until the halt of the movement of the light receiving part at the time when the movement of the light receiving part is halted and the data is processed by the use of the held time series data after the restart of the movement of the light receiving part and the time series data obtained after the restart, there is no need of obtaining the time series data again so that it is possible to shorten the time period required for processing the data.

With an arrangement that the above-mentioned control part is so configured that the control part ceases the analysis of the particles by halting the movement of the light receiving part in case that the overcurrent detecting part detects the overcurrent more than or equal to the predetermined number of times, it is possible to stop continuing to continuously produce the overcurrent in the light receiving part in case that a condition is intentionally attained that, for example, the overcurrent might be produced in the light receiving part clearly due to an impertinent condition setting.

If the data processing part comprises a plurality of multibit counters that are arranged in parallel and that count a number of pulses obtained by the electric current signal received in a state that a gate is open, a correlator that holds a time series data of the number of pulses until the halt of the movement of the light receiving part at a time when the movement of the light receiving part is halted and that restarts making auto-correlation data based on the held time series data of the number of pulses and the time series data of the number of pulses after the restart of the movement of the light receiving part, and a calculating part that calculates particle diameter distribution of a particle group based on the auto-correlation data obtained by the correlator, it is possible to shorten a time required for measuring the particle diameter distribution without wasting the previous time series data of the pulse number compared with a conventional device even though a big diameter particle is included in the sample and the overcurrent detecting part detects the overcurrent.

Effect of the Invention

In accordance with this invention, in case that the overcurrent detecting part detects the overcurrent, it is possible to avoid the light receiving part from getting damaged or degraded. In addition, since the time for conducting a measurement anew becomes unnecessary, it is possible to shorten the time required for measurement in this situation.

BEST MODES OF EMBODYING THE INVENTION

One embodiment of this invention will be explained with reference to drawings.

A particle diameter distribution measurement device 1 as being a particle analytical device in accordance with this embodiment gradually grows particles, is used together with a micro particle producing device (not shown in drawings) that produces single nano particles, and is utilized for measuring a particle diameter distribution and for controlling the particle diameter during a process of growing the particles.

Figure 1:
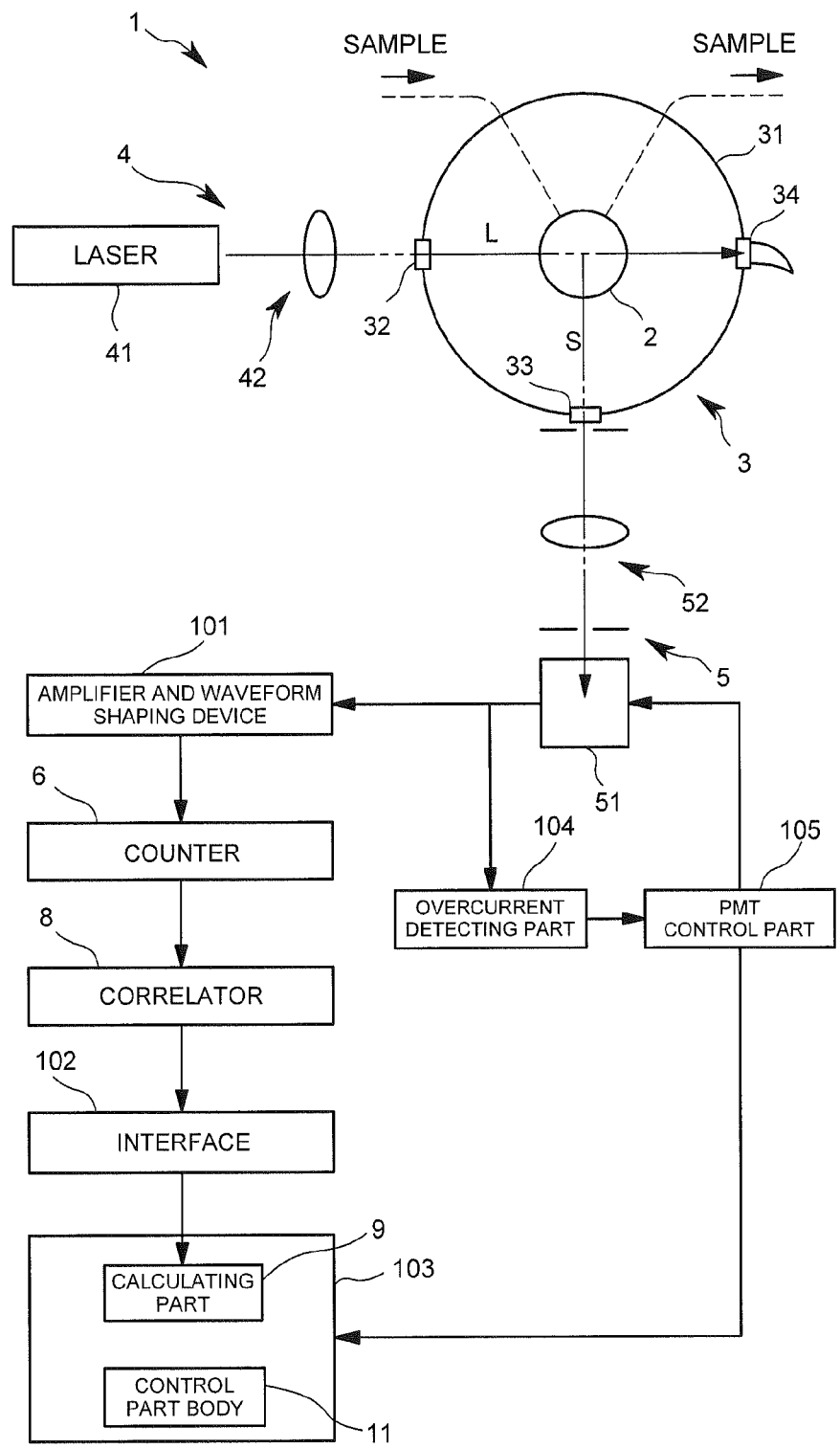
FIG. 1 is a pattern overall view showing a particle diameter distribution measurement device in accordance with one embodiment of this invention.

First, a fundamental configuration of this particle diameter distribution measurement device 1 will be explained. The particle diameter distribution measurement device 1 comprises, as shown in FIG. 1, a transparent cell 2 that houses a sample wherein a particle group is diffused in a dispersion media such as water, a bus 3 inside of which the cell 2 is oil-immersed, a light irradiation part 4 that irradiates laser light (L) on the sample through the bus 3 from outside of the cell 2, a light receiving part 5 that receives the scattered light (S) emitted from the particle group on which the laser light (L) is irradiated and that outputs an electric current signal in accordance with a photon number, a plurality of counters 6 that count a number of pulses (hereinafter called as a pulse number) obtained from the electric current signal that is received in a state that a gate is open, a control part 7 that sets a period of time when the gate of each counter 6 is open to be identical each other and that gives the timing when the gate opens to each counter 6 so as to be untimely, a correlator 8 that produces auto-correlation data based on time series data of the pulse number obtained by each counter 6, and a calculating part 9 that calculates particle diameter distribution of the particle group based on the auto-correlation data obtained by the correlator 8.

Each part will be explained.

The cell 2 is of a flow cell type that is hollow made of a transparent wall, and inside of which the sample flows unidirectionally at a pace within a predetermined speed. The sample is sent from the above-mentioned micro particle producing device, introduced into inside of the cell 2 through an introducing port and then discharged through a discharging port.

The bus 3 is made of a hollow wall body 31 that can be sealed and a transparent liquid having a refraction factor identical to or approximate to that of the cell 2 that is filled inside of the wall body 31, and the cell 2 is housed at a center of inside of the bus 3. The wall body 31 is made of, for example, an opaque metal and a laser light window 32 and a scattered light window 33 in order to transmit the light are arranged on an optical path of the laser light (L) and an optical path of the scattered light (S) respectively. A code 34 arranged on the wall body 31 opposite to the laser light window 32 is a light stopper to restrain the reflection by attenuating the laser light (L) passing the cell 2. In this embodiment, the optical path of the laser light (L) does not coincide with the optical path of the scattered light (S) (each optical path is orthogonal in FIG. 1), however, each optical path may coincide each other.

The light irradiation part 4 comprises, for example, a semiconductor laser 41 as being a light source, and a laser light guide mechanism 42 that condenses the laser light (L) irradiated from the semiconductor laser 41 on a light irradiation area (for example, a center) locating inside of the cell 2 through the laser light window 32. The laser light guide mechanism 42 consists of, for example, a light condensing lens or the like.

The light receiving part 5 comprises a photoelectron multiplier (PMT) 51 as being a light detector, and a scattered light guide mechanism 52 that introduces the scattered light (S) passing the scattered light window 33 into the photoelectron multiplier 51. The photoelectron multiplier 51 outputs an electric current signal in accordance with a photon number of the incident light. The scattered light guide mechanism 52 is a mechanism wherein a lens is arranged between a pair of pinholes.

Figure 2:
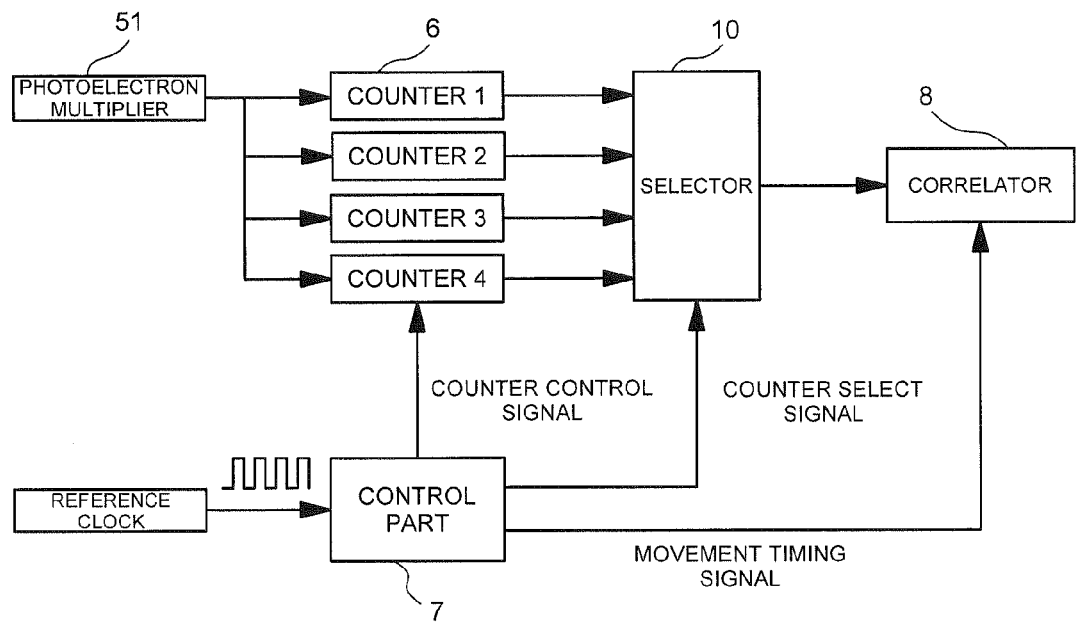
FIG. 2 is a hardware configuration view showing a hardware configuration in accordance with this embodiment.
Figure 3:
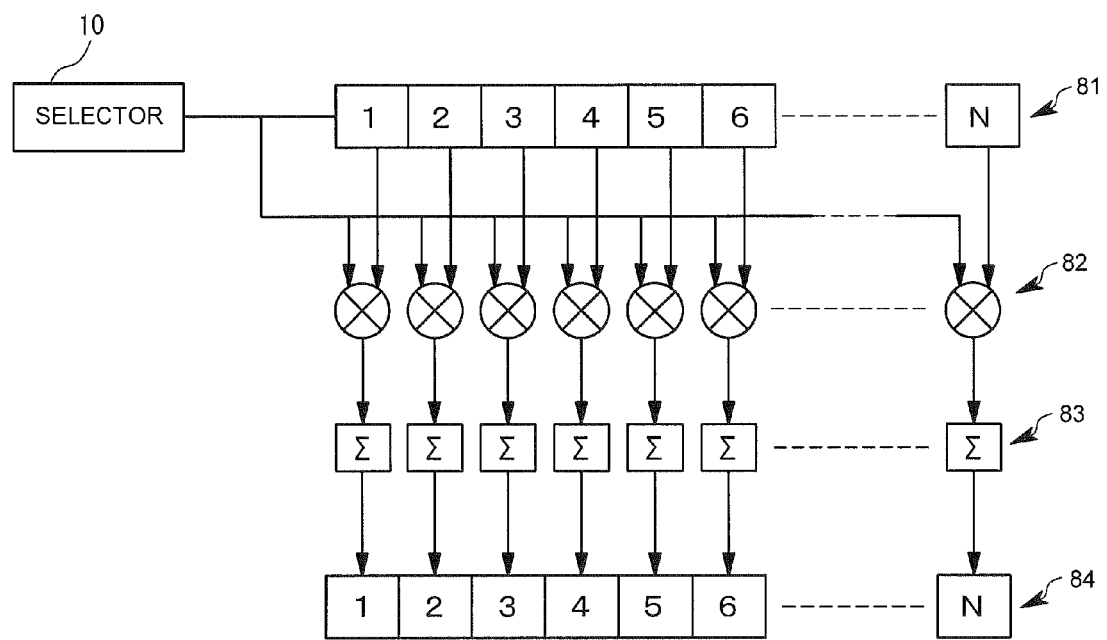
FIG. 3 is a hardware configuration view showing the hardware configuration in accordance with this embodiment.
Figure 4:
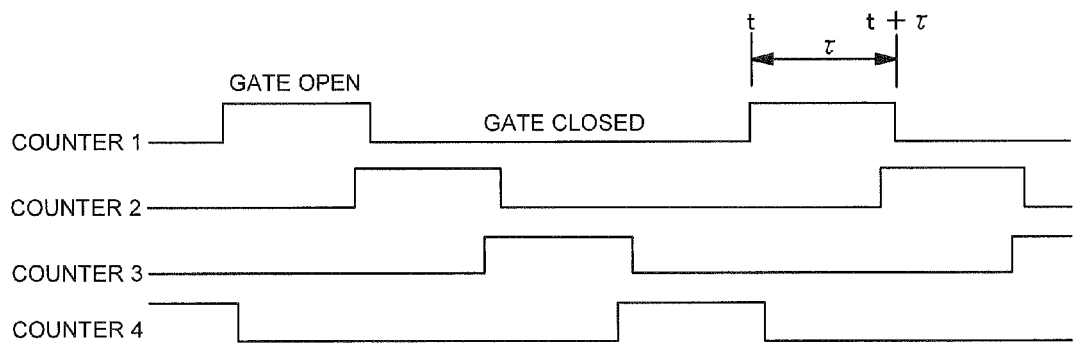
FIG. 4 is a timing chart showing open/close of a gate in this embodiment.

The electric current signal from the light receiving part 5 is, as shown in FIG. 2 and FIG. 3 in detail, processed (waveform is shaped) into a pulse through an amplifier and a waveform shaping device 101, and the pulse is input to a plurality (four, in this embodiment) of multibit (for example, 8 bits) counters 6 that are arranged in parallel. A gate (not shown in drawings) is provided for each of the counters 6, and the pulse is received in a state that the gate is open and a number of the pulse, namely a pulse number is counted. A timing of opening the gate and a time period while the gate is open are controlled by a counter control signal sent by the control part 7. More concretely, as shown in FIG. 4, it is so controlled that the time period (shown by τ in FIG. 4) while the gate of each counter 6 is open becomes equal and the timing (shown by t in FIG. 4) to open each gate is repeated sequentially with a certain time period deviated for each of the counters 6. In addition, a time when the gate of one counter 6 opens slightly overlaps a time when the gate of the next counter 6 opens so that at least a gate of either one of the counters 6 opens on a constant basis, which enables counting the number of the pulses with considering a dead time that fails monitoring between a time when the gate of one counter 6 opens and a time when the gate of the next counter 6 opens. The number of the pulses counted by each counter 6 is sent to a selector 10 while the gate of the counter 6 itself is closed and then sent to the correlator 8 sequentially by a counter select signal from the control part 7. In the meantime, the counted number is reset. In this embodiment, the minimum time while the gate opens is 10 ns, and the sampling at the maximum 100 MHz can be conducted.

Figure 5:
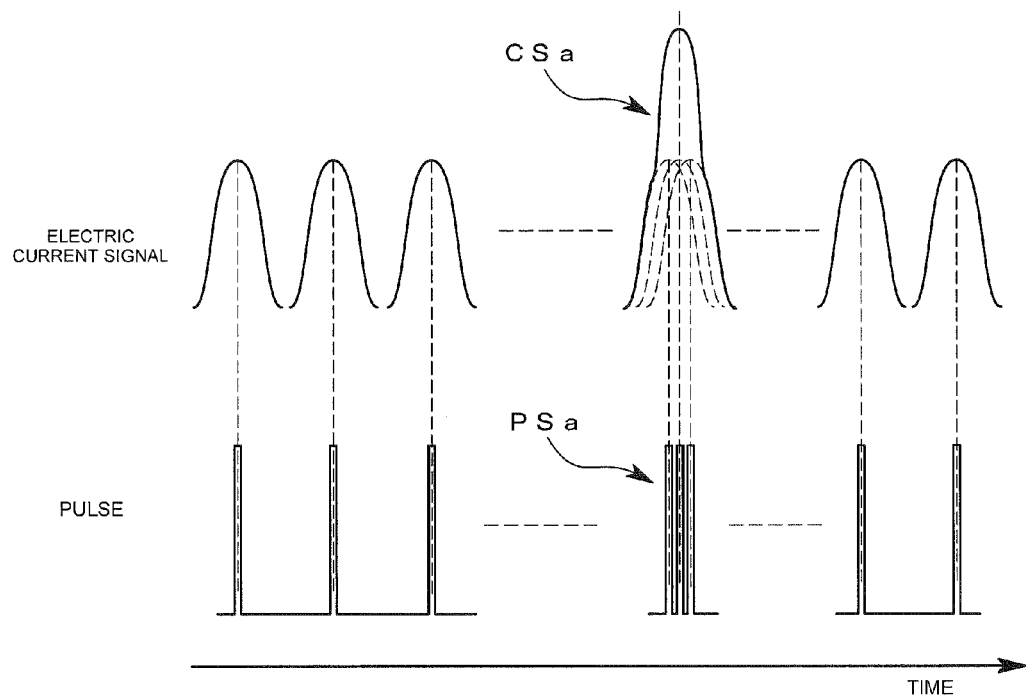
FIG. 5 is a waveform view showing a relationship between an electric current signal waveform and a pulse in this embodiment.

The pulse is obtained by amplifying the electric current signal shown in FIG. 5, followed by shaping the waveform of the amplified electric current signal by the use of the amplifier and the waveform shaping device 101. For example, the amplified electric current signal is transformed into a pulse that rises at a timing when the amplified electric current signal rises.

The correlator 8 obtains the auto-correlation data based on the time series data of the pulse number sent in series at certain intervals from each counter 6 through the selector 10. Concretely, the correlator 8 comprises a shift register 81 of multiple channels (N channel), a multiplier 82, an accumulator 83 and a storage memory 84 as shown in FIG. 3. The correlator 8 multiplies the pulse number data stored in each channel of the shift register 81 while shifting with the latest pulse number data by the use of the multiplier 82, and accumulates each of the obtained multiplied data by the use of the accumulator 83 and then stores the accumulated data in the storage memory 84 as the auto-correlation data. An operation timing such as a shift timing of the shift resister 81, an arithmetic timing of the multiplier 82, and an arithmetic timing of the accumulator 83 is controlled by an operation timing signal from the control part 7.

Since an input signal in a configuration from the counter 6 to the correlator 8 is a digital value as being a photon pulse number, all digital configuration by the use of a discrete circuit or a programmable logic circuit can be established, thereby enabling better suited for downsizing with high reliability and accuracy at low cost.

A function of the calculating part 9 is served by an information processing unit 103 such as a computer to which predetermined software is installed. The calculating part 9 obtains auto-correlation data stored in the storage memory 84 of the correlator 8 after termination of the measurement by the count of "N" times and calculates particle diameter distribution of the sample according to the known predetermined algorithm. A calculated result is displayed on, for example, a display.

Furthermore, a control part body 11 is arranged for the information processing unit 103 by installing software. The control part body 11 outputs an instruction signal automatically or based on an input instruction by an operator, controls the laser power by controlling the light irradiation part 4 and controls the time period while the gate is open and the timing of opening the gate by controlling the control part 7 by the use of a particle diameter to which the measurement is expected, a flow rate of the sample flowing in the flow cell 2, and a concentration, a color and a refraction factor of the particles as parameters in order to optimize the measurement condition.

For example, while the gate is open, the particle diameter to which the measurement is expected or the flow rate of the sample flowing in the flow cell 2 is set as the parameter. More concretely, the smaller the particle diameter is or the faster the flow rate is, the smaller the time period while the gate is open is set. It is a matter of course that the timing to open the gate is changed in accordance with the time period while the gate is open.

In addition, since the counter 6 is of limited bits, if the counted number of the photon is too big, an overflow generates. Conversely, if the counted number of the photon is too small, an S/N ratio descends so that the measurement accuracy is degraded. As a result, the laser power and the time period while the gate is open are set so as to enable an appropriate count with the concentration, the color and the refraction factor of the particle set as the parameter. Furthermore, it is also possible to set the time period while the gate is open in accordance with scaling of the particle diameter or a change rate of the particle diameter.

As mentioned, in accordance with the particle diameter distribution measurement device 1 of this embodiment having the above-mentioned arrangement, since multiple multibit counters 6 are arranged in parallel, it is possible to count the photon number at a high speed similar to the pulse based on the electric current signal obtained by the photoelectron multiplier 51 without failing to count, and to measure the diameter of the particle group that flows together with the dispersion media before its environment changes. As a result of this, the particle diameter distribution can be measured with assuming that the state is steady and equilibrium.

Furthermore, in this embodiment provided are an overcurrent detecting part 104 that detects that the overcurrent flows in the light receiving part 5 based on the electric current signal output by the light receiving part 5 and a PMT control part 105 that halts a movement of the light receiving part 5 in case that the overcurrent detecting part 104 detects the overcurrent, and that restarts the movement of the light receiving part 5 at a time when a predetermined time period passes after the movement of the light receiving part 5 is halted.

The overcurrent detecting part 104 compares an electric current value of an electric current signal output by the photoelectron multiplier 51 with a previously set predetermined electric current value. Based on a result of the comparison, in case that the electric current value of the electric current signal is more than or equal to the predetermined electric current value, the overcurrent detecting part 104 detects that the overcurrent flows in the photoelectron multiplier 51. The predetermined electric current value is set at a value smaller than an electric current value at which the photoelectron multiplier 51 is electrically broken. In order to detect the overcurrent, the overcurrent detecting part 104 measures the electric current value of the electric current signal by the use of a wave height value of the electric current signal. In case that the overcurrent is detected, the overcurrent detecting part 104 outputs the overcurrent detecting signal to the PMT control part 105.

The PMT control part 105 usually applies a voltage to each electrode of the photoelectron multiplier 51 and cuts off the voltage applied to the photoelectron multiplier 51 in case that the overcurrent detecting signal is received from the overcurrent detecting part 104. In case that the voltage applied to the photoelectron multiplier 51 is cut-off, the PMT control part 105 measures an elapsed time from the time when the voltage is cut-off. At a time when the elapsed time reaches the above-mentioned predetermined time, the PMT control part 105 applies the voltage to the photoelectron multiplier 51 in order to restart the movement of the photoelectron multiplier 51. The predetermined time is set based on, for example, a sufficient time to disappear the scattered light due to the overlarge particles.

Furthermore, the PMT control part 105 acts to cease the particle distribution measurement in case that the number of times when the overcurrent detecting signal is received is more than or equal to a predetermined number during one measurement of the particle diameter distribution.

Next, during the measurement of the particle diameter distribution of the sample, in case that the overcurrent detecting part 104 detects that the overcurrent flows in the photoelectron multiplier 51 because the intensity of the scattered light becomes high due to mixture of foreign material whose particle diameter is big in the sample or the photon is mixed into the photoelectron multiplier 51 almost at the same time, the particle diameter distribution measurement device 1 acts as follows.

More specifically, as shown by a code (CSa) in FIG. 5, when the overcurrent detecting part 104 detects the overcurrent in the photoelectron multiplier 51 based on the electric current signal whose wave height value output by the photoelectron multiplier 51 becomes high, the PMT control part 105 receives the overcurrent detecting signal and instantly cuts off the voltage applied to the photoelectron multiplier 51. As a result of this, the photoelectron multiplier 51 halts the movement. Accordingly, the electric current signal is not output to the amplifier and the wave form shaping part 101. At a time when the movement of the photoelectron multiplier 51 is halted, the PMT control part 105 counts a number of times when the overcurrent detecting signal is received and then stores its result.

The PMT control part 105 transmits the halt of the movement of the photoelectron multiplier 51 due to the overcurrent to the information processing unit 103. Then the information processing unit 103 holds (temporarily stores) the time series data of all of the pulse number until the halt of the movement of the photoelectron multiplier 51.

Later, after the predetermined time period, the PMT control part 105 restarts the movement of the photoelectron multiplier 51 by applying the voltage to the photoelectron multiplier 51 and transmits that the movement of the photoelectron multiplier 51 is restarted to the information processing unit 103. Then, the information processing unit 103 restarts the movement of the counter 6, the correlator 8 and the calculating part 9 in synchronized with the photoelectron multiplier 51. Accordingly, the pulse is input to the counter 6 through the amplifier and the waveform shaping device 101 from the photoelectron multiplier 51, and the calculating part 9 calculates the particle diameter distribution of the sample. In this case, at a time when the movement of the photoelectron multiplier 51 is halted, the time series data of the pulse number held by the information processing unit 103 is used for calculation of the particle diameter distribution of the sample after the restart of the movement of the photoelectron multiplier 51.

As mentioned above, in case that the overcurrent flows in the photoelectron multiplier 51, it is possible to avoid the photoelectron multiplier 51 from getting damaged or degraded by halting the movement of the photoelectron multiplier 51. In addition, there is no need of taking the data of the time series data of the pulse number again from the first anew by making the counter 6 hold the time series data of the previous pulse number in case that the overcurrent of the photoelectron multiplier 51 is detected and by using the time series data for calculation of the particle diameter distribution of the sample in case that the movement of the photoelectron multiplier 51 is restarted after a predetermined period of time. As a result, it is possible to reduce the entire time required for calculation of the particle diameter distribution.

Figure 6:
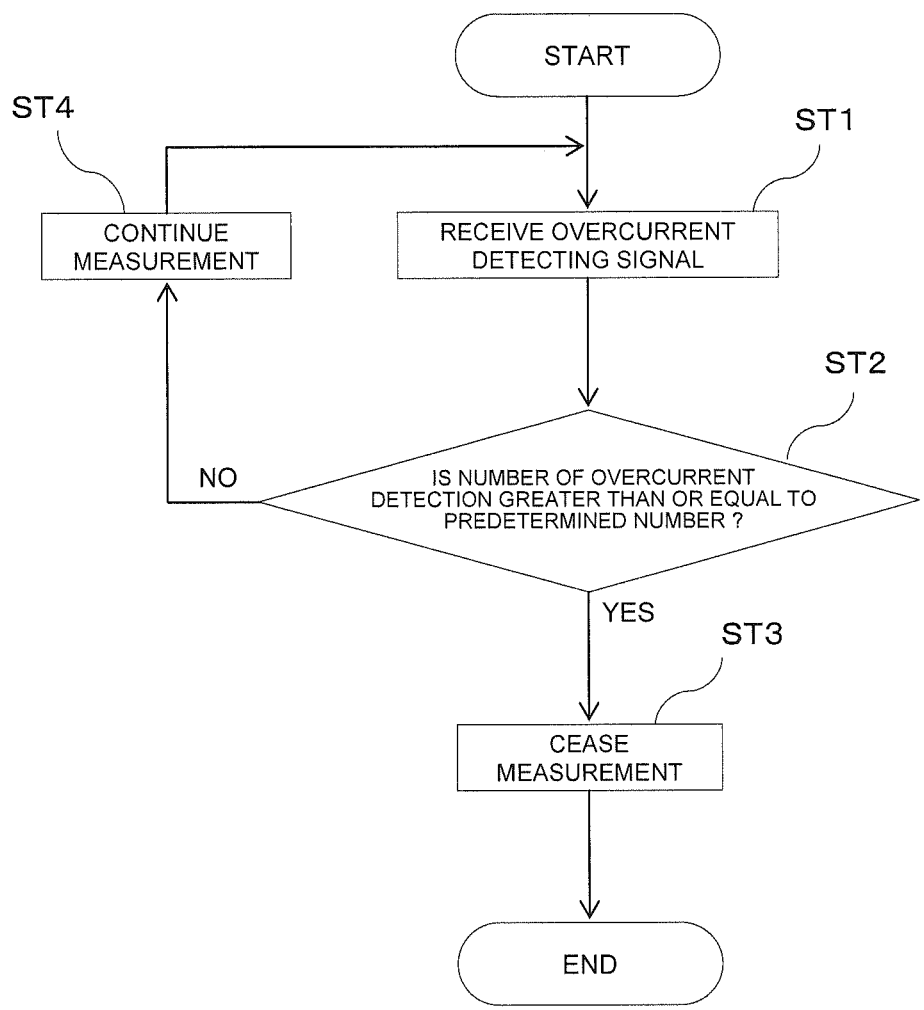
FIG. 6 is a flow chart showing a control movement in this embodiment.

After this process, in case that the overcurrent detecting part 104 detects the overcurrent, the above-mentioned control is repeated. However, in case that a number of times when the PMT control part 105 receives the overcurrent detecting signal becomes more than or equal to a predetermined number during one measurement of the particle diameter distribution, the PMT control part 105 forcibly ceases the operation of the particle diameter distribution measurement device 1. More specifically, as shown in FIG. 6, the PMT control part 105 receives the overcurrent detecting signal and stores the number of times when the overcurrent detecting signal is detected (Step ST1). The PMT control part 105 judges whether the stored number of times when the overcurrent detecting signal is received is more than or equal to the predetermined number during one measurement of the particle diameter distribution (Step ST2). In case that the stored number is judged to be more than or equal to the predetermined number, the PMT control part 105 acts on the information processing unit 103 to cease the measurement of the particle diameter distribution (Step ST3). In case that the stored number is less than the predetermined number, the measurement of the particle diameter distribution is continued (Step ST4).

As mentioned, in case that the stored number of times when the overcurrent detecting signal is received, namely, the stored number of times when the overcurrent generates is more than or equal to the predetermined number, the PMT control part 105 ceases to apply the voltage to the photoelectron multiplier 51 and resets the counter 6 and the correlator 8, and then outputs the instruction to cease the measurement of the particle diameter distribution to the information processing unit 103 in order to initialize the particle diameter distribution measurement device 1 in a state prior to the initiation of the measurement of the particle diameter distribution.

As mentioned, in case that a condition that the overcurrent is quite capable of flowing into the photoelectron multiplier 51 is intentionally attained by ceasing the particle diameter distribution measurement, it is possible to stop continuously flowing the overcurrent into the photoelectron multiplier 51. Accordingly, it is possible to avoid the photoelectron multiplier 51 from getting damaged or degradated.

The present claimed invention is not limited to the above-mentioned embodiment.

In the above-mentioned embodiment, the overcurrent detecting part 104 is explained as detecting the overcurrent by means of the wave height value of the electric current signal output by the photoelectron multiplier 51, however, the overcurrent detecting part 104 may count a pulse number per unit time wherein the pulse is obtained by shaping the waveform of the electric current signal and may detect the overcurrent when the pulse number exceeds the predetermined number. The waveform of the pulse in this case will be shown by a code (PSa) in FIG. 5. In this case, the counted result by the counter 6 may be diverted.

Figure 7:
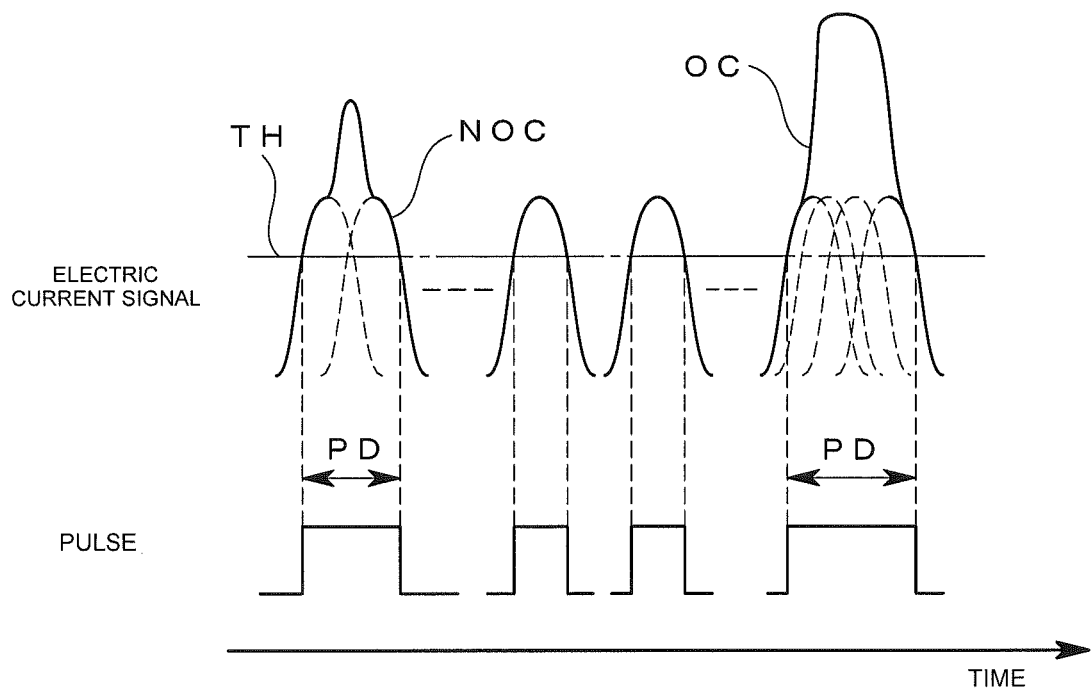
FIG. 7 is a waveform view showing a relationship between an electric current signal waveform and a pulse in accordance with a modified example of an overcurrent detection in this embodiment.

In addition, the overcurrent may be detected based on a time period when the electric current signal output by the photoelectron multiplier 51 is continuous. More concretely, as shown in FIG. 7, in case that the photoelectron multiplier 51 continuously outputs the electric current signal and each of the electric current signals superposes with sliding the time when the electric current signal becomes a peak, the overcurrent is detected based on the time period when the electric current signal that becomes more than or equal to a predetermined threshold level (TH) is continuous. Namely, the waveform of the electric current signal (OC) output by the photoelectron multiplier 51 is shaped based on the predetermined threshold level (TH), a rectangular wave obtained by shaping the waveform of the electric current signal (OC) or duration of the pulse (PD) (hereinafter called as the pulse duration), namely, a time period from a rise time to a fall time of the rectangular wave or the pulse is measured, and the measured pulse duration (PD) and a judge time to judge the overcurrent are compared. Based on the result of the comparison, in case that the measured pulse duration (PD) is more than or equal to the judge time, the overcurrent is detected. In case that the electric current signal is a signal shown by a code (NOC) in FIG. 7 and the pulse duration (PD) is less than the judge time, the overcurrent is not detected even though the electric current signals are superimposed with each time of the peaks shifted.

In the above-mentioned embodiment, the PMT control part is configured to measure the elapsed time from the halt of the movement of the photoelectron multiplier 51, however, the PMT control part 105 may be integrated into the information processing unit 103. The information processing unit 103 may measure the elapsed time. More specifically, the information processing unit 103 may judge whether or not the measured elapsed time is more than or equal to the predetermined time and in case that the elapsed time is judged to be more than or equal to the predetermined time, the information processing unit 103 may instruct a voltage control part (circuit) that controls the electric voltage of the photoelectron multiplier 51 to restart the movement of the photoelectron multiplier 51 and simultaneously may instruct the counter 6 to count the pulse number.

Similarly, a number of receiving the overcurrent detecting signal counted by the PMT control part 105, namely a number of times ceasing the movement of the photoelectron multiplier 51 due to the overcurrent is counted by the information processing unit 103 instead of the PMT control part 105. In this case, the information processing unit 103 judges that the number of ceasing the movement is more than or equal to the predetermined number and an operation of the particle diameter distribution device 1, namely the measurement of the particle diameter distribution is ceased. With this arrangement of the information processing unit 103, it is possible to simplify the configuration of the device.

In the above-mentioned embodiment, the particle diameter distribution measurement device is explained, however, this invention may be applied to a device that measures a zeta potential by the use of the photoelectron multiplier.

The present claimed invention is not limited to the above-mentioned embodiment and it is a matte fo coutse that the present claimed invention may be variously modified without departing from a spirit of the invention.

EXPLANATION OF CODES

1 . . . particle diameter distribution measurement device
4 . . . light irradiating part
5 . . . light receiving part
6 . . . counter
8 . . . correlator
9 . . . calculating part
104 . . . overcurrent detecting part
105 . . . PMT control part

The invention claimed is:

1. A particle analytical device comprising
a light irradiation part that irradiates the light toward a particle group that moves in a dispersion medium,
a light receiving part that receives the scattered light emitted from the particle group on which the light from the light irradiation part is irradiated and that outputs an electric current signal,
a data processing part that processes data concerning particle analysis based on time series data of a number of pulses obtained by the electric current signal output by the light receiving part,
an overcurrent detecting part that detects flowing of an overcurrent in the light receiving part based on the electric current signal output by the light receiving part, and
a control part that halts an operation of the light receiving part in a case where the overcurrent detecting part detects the overcurrent, and that restarts the operation of the light receiving part after a predetermined time passes from a time when the operation of the light receiving part is halted, wherein
the data processing part holds the time series data until the halt at a time when the operation of the light receiving part is halted and processes the data, after the operation of the light receiving part is restarted, by the use of the held time series data and the time series data obtained after the restart.

2. The particle analytical device described in claim 1, wherein
the control part stops data processing by the data processing part by halting the operation of the light receiving part in a case where the overcurrent detecting part detects the overcurrent more than or equal to a predetermined number of times.

3. The particle analytical device described in claim 1, wherein
the data processing part comprises a plurality of multibit counters that are arranged in parallel and that count the number of the pulses obtained by the electric current signal received in a state that a gate is open,
a correlator that holds time series data of the number of pulses until the halt of the operation of the light receiving part at a time when the operation of the light receiving part is halted and that makes auto-correlation data based on the held time series data of the number of pulses and the time series data of the number of pulses after the restart of the operation of the light receiving part, and a calculating part that calculates a particle diameter distribution of a particle group based on the auto-correlation data obtained by the correlator.

4. A method for analyzing particles by making use of the particle analytical device described in claim 1, wherein operation of the light receiving part is halted in a case where the overcurrent flowing in the light detecting part is detected based on the electric current signal output by the light receiving part, the time series data until the halt of the operation of the light receiving part is held in a case where the operation of the light receiving part is halted, the operation of the light receiving part is restarted after the predetermined time passes from the time when the operation of the light receiving part is halted, and the data is processed based on the held time series data and the time series data obtained after the restart after the operation of the light receiving part is restarted.

* * * * *